United States Patent [19]

Altholz et al.

[11] Patent Number: 5,395,675
[45] Date of Patent: Mar. 7, 1995

[54] PROTECTIVE COVERING FOR SELECT AREAS OF THE SURFACE ANATOMY OF THE BODY

[76] Inventors: Charles K. Altholz, 1830 Spruce Ave., Highland Park, Ill. 60035; Barry Faldner, 206 Hibbard Rd., Wilmette, Ill. 60091; Barry Sufrin, 540 Drexel, Glencoe, Ill. 60022

[21] Appl. No.: 956,371

[22] Filed: Oct. 5, 1992

[51] Int. Cl.6 .................................. B32B 9/00
[52] U.S. Cl. .............................. 428/195; 428/45; 428/47; 428/71; 428/76; 428/88; 428/97; 428/99; 602/53; 602/54; 604/307; 604/308; 604/389
[58] Field of Search ............ 428/195, 45, 76, 47, 428/325, 71, 88, 97, 99; 602/42, 44, 48, 46, 54, 58, 53; 604/307, 305

[56] References Cited

U.S. PATENT DOCUMENTS

| | | | |
|---|---|---|---|
| 2,221,758 | 11/1940 | Elmquist | 128/154 |
| 3,288,139 | 9/1964 | Goodman | 602/48 |
| 3,425,412 | 2/1969 | Pope | 128/156 |
| 3,528,416 | 9/1970 | Chamberlain | 128/154 |
| 3,645,835 | 2/1972 | Hodgson | 161/146 |
| 3,954,105 | 5/1976 | Nordby et al. | 128/275 |
| 4,295,987 | 10/1981 | Parks | 252/194 |
| 4,341,208 | 7/1982 | Gordon | 128/156 |
| 4,399,816 | 8/1983 | Spangler | 128/154 |
| 4,413,621 | 11/1983 | McCracken et al. | 128/156 |
| 4,485,809 | 12/1984 | Dellas | 128/156 |
| 4,517,972 | 5/1985 | Finch, Jr. | 128/156 |
| 4,641,643 | 2/1987 | Greer | 128/156 |
| 4,846,164 | 7/1989 | Martz | 128/155 |
| 4,906,240 | 3/1990 | Reed et al. | 604/307 |
| 4,917,112 | 4/1990 | Kalt | 128/156 |
| 4,935,087 | 6/1990 | Gilman | 156/251 |
| 5,061,258 | 10/1991 | Martz | 604/307 |
| 5,092,323 | 3/1992 | Riedel et al. | 602/54 |
| 5,106,629 | 4/1992 | Cartmell et al. | 424/445 |

Primary Examiner—Patrick J. Ryan
Assistant Examiner—Abraham Bahta
Attorney, Agent, or Firm—Barry W. Sufrin

[57] ABSTRACT

A protective covering for select areas of the surface anatomy of the body having incisions, wounds, injuries or other delicate features requiring protection from moisture or trauma for limited periods of time during external application of water or aqueous solutions including a waterproof flexible membrane, a window to aid in positioning over the select areas and means for affixing the membrane without adhering to the incisions, wounds, injuries or delicate features requiring protection.

21 Claims, 2 Drawing Sheets

PROTECTIVE COVERING FOR SELECT AREAS OF THE SURFACE ANATOMY OF THE BODY

BACKGROUND OF THE INVENTION

The present invention relates generally to coverings for select areas of the surface anatomy of the body. More particularly, the present invention relates to water-impermeable protective coatings for select areas of the surface anatomy of the body having incisions, wounds, external injuries, or other external features requiring protection from moisture or trauma for limited periods of time during application of eater or aqueous solutions.

Patients have a common complaint following procedures or treatments producing or dealing with incisions, wounds, injuries or other conditions requiring protection from moisture in order to promote healing and control bacterial growth. Their complaint is the discomfort and inconvenience arising from the prohibition against bathing or showering in order to avoid inadvertently wetting those areas. Additionally, notwithstanding the prohibition against wetting such sensitive areas, these patients may nevertheless require water-based therapies for, e.g., physical therapy or burn treatment.

Unfortunately, conventional bandages, even if waterproof, are ill-suited for protecting such sensitive areas. First, conventional bandages tend to adhere to wound areas and to harm wounds when removed. Second, even if the adhesive or other wound-adhering materials are removed from conventional bandages in the area of the wound to be covered, it is difficult to orient the bandages with the non-adhesive portion properly positioned over the wound. Third, using conventional bandages, it is difficult, if not impossible, to observe the wound, in order to take action immediately, if moisture enters an area which must be protected. Also, conventional bandages that provide limited protection from moisture are uncomfortable to apply and remove for protection from periodic contact with water as a result of either personal hygiene or water-based treatments. Finally, conventional bandages do not provide protection from inadvertent trauma to the protected site.

SUMMARY OF THE INVENTION

The present invention provides a protective covering for select areas of the surface anatomy of the body having incisions, wounds, injuries, or other features requiring protection from moisture for limited periods of time during contact or external treatment with water or aqueous solutions. The covering includes a waterproof, flexible member having means for viewing across the membrane and water-impermeable means for affixing the covering to the select areas of the surface of the body without adhering to the incisions, wounds, injuries, or other features. The protective covering may be dispensed as a single generally flat member or it may be part of a series of interconnected protective covering wound on a spool and designed to be removed one-by-one, by pulling on a tab.

The viewing means may be transparent or translucent, in order to facilitate placement of the protective covering over the wound site. The viewing means may be in any shape, although an oval shape is preferred to facilitate centering over elongated wound sites The viewing means may be rigid or "semi-rigid" in order to protect the wound site from trauma By "semi-rigid", we mean resilient yet resistant enough to deformation to withstand blows without collapsing onto the wound site. The viewing means preferably will be dome-shaped to maintain a protected space above the protected site. Alternatively, means may be provided for spacing the viewing means from the protection site, also to prevent trauma thereto.

The viewing means may be chosen from among films and rigid and semi-rigid forms of the following commonly available moisture impermeable materials: polyester, UPVC, extruded plastic, polypropylene, polyethylene, nylon, and vinyl plastic. Other conventionally available—preferably hypoallergenic—flexible, semi-rigid and rigid water-impermeable materials may, of course, be used.

In one important embodiment of the invention, the viewing means is adapted to permit air and water vapor to pass from the side facing the area requiring moisture protection, without admitting water or water vapor in the opposite direction. This facilitates release of moisture generated by the body, which is preferably released from the wound site, to encourage healing and minimize infection.

The affixing means may be an adhesive-coated flexible substrate. The preferred adhesives include hypoallergenic pressure-sensitive acrylic and rubber adhesive formulations. It is preferred that the adhesives present adequate adhesion for securement, yet that they can be removed with minimal skin trauma. It is preferred that the flexible substrate be conformable to the contours of the select areas being covered and that it move with the body, in order to insure the reliability of the moisture seal. The flexible substrate may be chosen from among: polyester film, UPVC film, extruded plastic, polypropylene film, polyethylene film, nylon film, and vinyl plastic film. In a preferred embodiment, the substrate will be no more than about 5 mils in thickness and have an elongation of at least about 100 percent.

Alternatively, the flexible substrate may be a foam-like material chosen from among the following: open-cell urethane foam, open-cell polyethylene foam, closed-cell vinyl foam, closed-cell elastomeric, and closed-cell acrylic foam. Such substrates should be at least about 25 mils in thickness. Preferably, these substrates will have a elongation of at least about 10 percent, in order to permit stretching with the body.

It is preferred that a visible portion of the substrate be brightly colored to alert the patient or the physical therapist to the presence of the water-sensitive site, so that it will be as little disturbed as possible. Also, the exposed surface may be texturized so that the patient or therapist will feel the presence of the protective covering to further prevent inadvertent rough treatment in the area.

In an alternative embodiment of the invention, an absorbent material is provided about the perimeter of the viewing means. The absorbent material should completely encircle the perimeter of the viewing means in order to take up any moisture which might pass through the affixing means. When an absorbent is used, it is most preferred that super polymer absorbent compositions be used, which absorb many times their weight in water and aqueous fluids. Such compositions are described, for example, in U.S. Pat. No. 4,295,987. In addition, an indicator may be provided which changes color upon entry of moisture to the protected area, to warn the patient that the protective coating must be promptly removed.

In yet another embodiment of the invention, a continuous band is attached to the skin adjacent the perimeter of the features to be protected from moisture. The band may be attached to the skin with a waterproof adhesive which will stick to the skin more tightly than to the waterproof flexible membrane. Alternatively, a waterproof coating is "painted" onto the skin in the form of a band surrounding the features to be protected from moisture. In either case, an alcohol-soluble adhesive or an alcohol-soluble coating may be used to facilitate later removal. If desired, hair, skin oils, etc., may be removed before placing the band, in order to insure a particularly watertight and secure attachment. The band provides a particularly desirable platform for facilitating removal and attachment of the waterproof flexible membrane without repeatedly tearing at the skin or at hairs in the skin surface. In fact, in yet another variation of the invention, the band may be metallic so that a waterproof flexible membrane having a magnetic strip about its perimeter may simply be attached by way of magnetic attraction or the band maybe chosen to facilitate attachment of the waterproof flexible membrane by electrostatic means.

It is an object of the present invention to provide a protective covering having the foregoing advantages. These and other objects of the invention are accomplished as illustrated in the drawings and as described in the detailed description which follows.

BRIEF DESCRIPTION OF THE DRAWINGS

The features of this invention which are believed to be novel are set forth with particularity in the appended claims. The invention, together with its objects and advantages, may best be understood by reference to the following description, taken in conjunction with the accompanying drawings, in which like reference numerals identify like elements in the several figures and in which:

DETAILED DESCRIPTION OF THE PREFERRED EMBODIMENTS

Figure 1A:
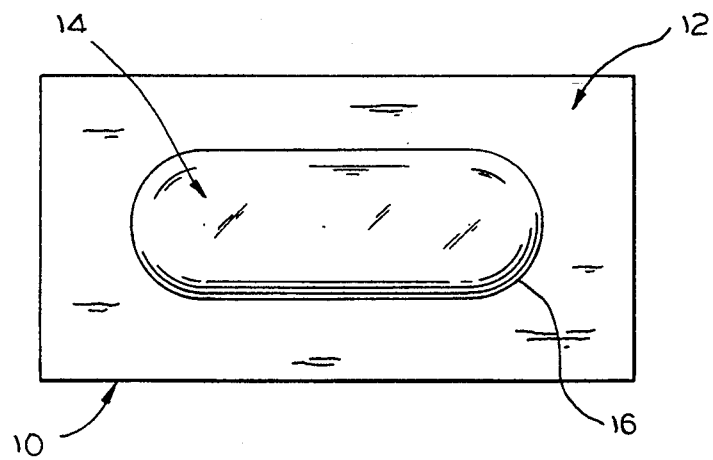
FIGS. 1A and 1B are respectively a top plan view and a perspective view of a protective covering in accordance with the present invention.
Figure 1B:
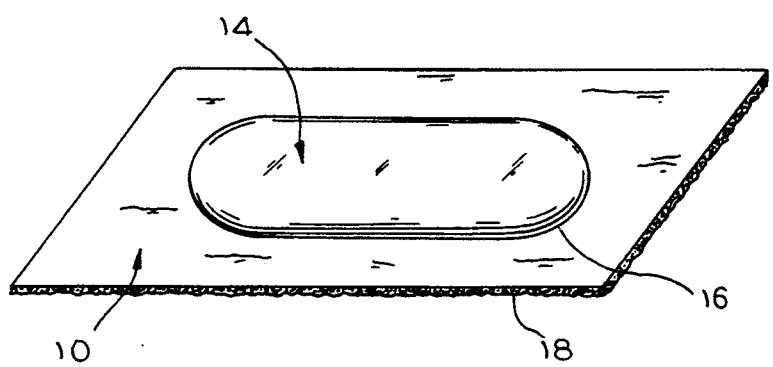
Figure 2A:
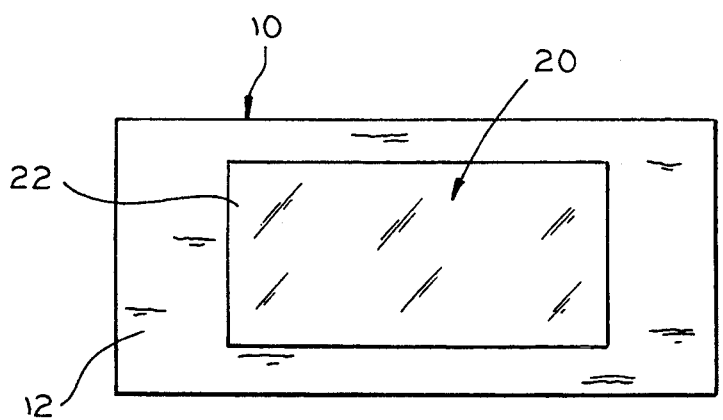
FIGS. 2A and 2B are respectively a top plan view and a perspective view of an alternative embodiment of the protective covering of the present invention.
Figure 2B:
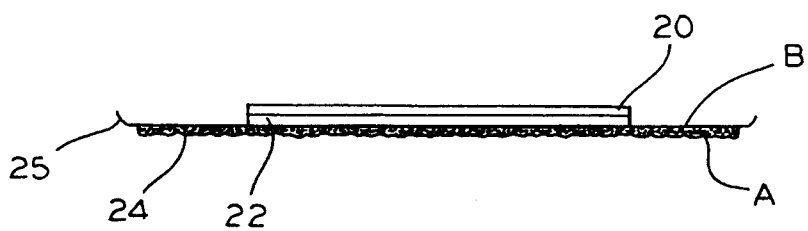

Turning first to FIGS. 1A and 1B, a protective covering 10 is illustrated, comprising a waterproof flexible member 12 having transparent viewing means centered in the flexible member. As best seen in FIG. 1B, the transparent viewing means in this embodiment is an oval rigid upstanding transparent plastic window 14 which is sealingly joined about its perimeter 16 to the flexible member which has an adhesive layer 18 spread across its bottom surface. In an alternative embodiment, as depicted in FIGS. 2A and 2B, the viewing means is a flat, semi-rigid member 20 supported by a rigid spacer 22. This semi-rigid member permits air and water vapor to pass from covered side A without admitting water or water vapor in the vicinity of the exposed side B, to thereby facilitate the release of moisture generated by the body.

Flexible substrate 12 in FIGS. 2A and 2B has an adhesive layer 24 which has adequate adhesion for securement, yet can be removed with minimal skin trauma. The adhesive layer, in the illustrated embodiment, does not reach to the outer edge of the flexible member, leaving a free lip 26 to facilitate removal of the protective coating, after it has served its intended function. When a similar free lip is provided about the outer edge of the flexible member of FIGS. 1A and 1B, the continuous curled edge will give the overall configuration a "derby-like" appearance.

Figure 3:
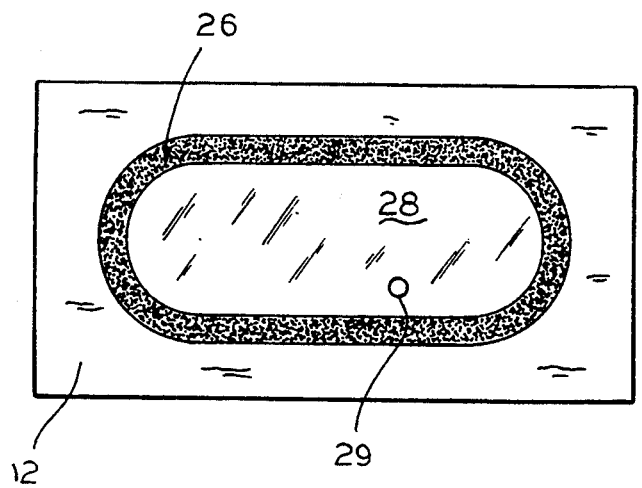
FIG. 3 is a top plan view of yet another alternative embodiment of the protective covering of the present invention.

In the embodiment illustrated in FIG. 3, an absorbent material 26 is placed about the perimeter of viewing means 28. This absorbent material picks up any moisture which might pass through the affixing means as well as moisture which may be generated by the body in the area intended to be protected from moisture. Additionally, a moisture indicator dot 29 is positioned along the edge of the viewing means. This dot will change color upon entry of moisture signalling that the protective covering needs to be removed.

Figure 4:
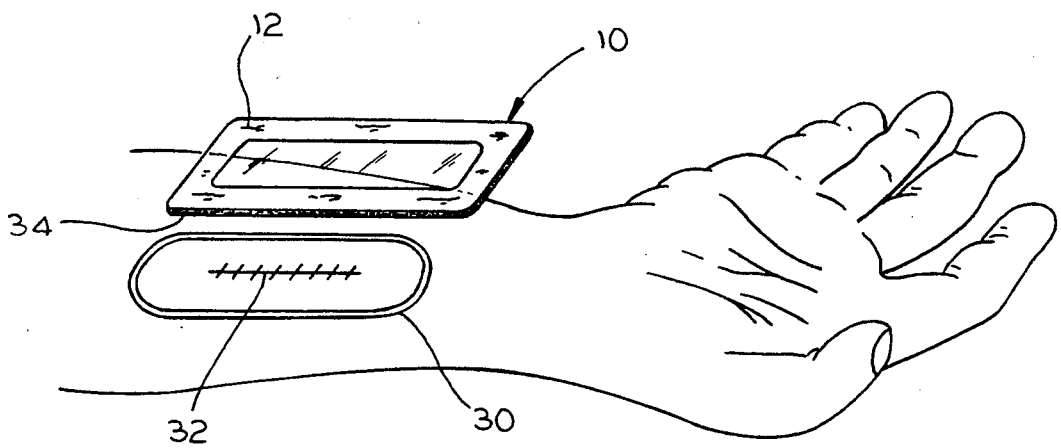
FIG. 4 is a top plan view of still another alternative embodiment of the protective covering of the present invention.

Yet another embodiment of the invention is illustrated in FIG. 4 wherein a continuous band 30 is attached to the skin of the forearm of a patient, adjacent to the perimeter of an incision 32 to be protected from moisture. Band 30 is attached to the skin with an adhesive which sticks more tightly than the water-proof flexible means. In this embodiment, the flexible means 12 has an adhesive 34 which will adhere less tightly to the protective coating than to the skin, thereby facilitating repeated removal and attachment without repeatedly tearing at the skin or hairs in the skin surface.

Figure 5:
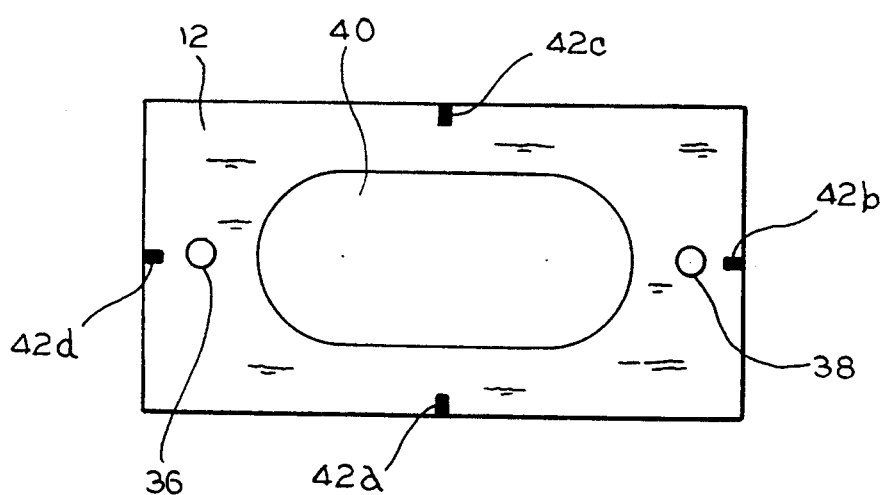
FIG. 5 is a top plan view of a further embodiment of the protective covering of the present invention.

Yet another embodiment of the invention is illustrated in FIG. 5. In this embodiment, two additional openings 36 and 38 are provided in the protective covering, evenly spaced from a clear window 40. Thus, placement of this protective covering will be particularly easy if markings are made on the skin of the patient in the vicinity of the area to be protected, so that holes 36 and 38 can be lined up with those markings before the protective coating is applied. Alternatively, markings can be provided along the edge of the covering, such as markings 42a, 42b, 42c, and 42d, so that such markings likewise can be lined up with markings placed on the skin, possibly by a surgeon following the closing of a sensitive incision, to facilitate the alignment of the covering and to insure that the non-adherent protective window is placed directly above the area which must be protected.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What we claim is:

1. A protective covering for select areas of the surface anatomy of the body having incisions, wounds, injuries, or other delicate features requiring protection from moisture during external application of water or aqueous solutions, comprising:

a flexible membrane providing protection from moisture having rigid or semi-rigid means for viewing across said membrane, said viewing means being sufficiently resistant to deformation to withstand blows without collapsing onto the wound site; and adhesive for affixing said membrane to the select areas of the surface anatomy of the body with said rigid or semi-rigid means overlying but spaced from the incisions, wounds, injuries, or other delicate features requiring protection from moisture to prevent adherence or injury thereto once the membrane is affixed.

2. The protective covering of claim 1 wherein said viewing means is transparent.

3. The protective covering of claim 1 wherien said flexible membrane has a texturized surface.

4. The protective covering of claim 1 herein said viewing means is adapted to permit air and water vapor to pass from the side facing the select areas of the surface anatomy of the body having incisions, wounds, injuries, or other delicate features requiring protection from moisture.

5. The protective covering of claim 1 wherein said affixing means is an adhesive coating in which said adhesive is chosen from the group consisting of hypoallergenic pressure sensitive acrylate and rubber adhesive formulations.

6. The protective covering of claim 1 in which said membrane is chosen from the group consisting of polyester film, UPVC film, extruded plastic, polypropylene film, polyethylene film, nylon film, and vinyl plastic film.

7. The protective covering of claim 1 in which said membrane is chosen from the group consisting of open-cell urethane foam, open-cell polyethylene foam, closed-cell vinyl foam, closed-cell elastomeric, and closed-cell acrylic foam.

8. The protective covering of claim 1 in which said membrane is no more than about 5 mils thick.

9. The protective covering of claim 1 in which said membrane is conformable to the contours of the select areas being covered.

10. The protective covering of claim 1 in which said membrane is at least about 25 mills thick.

11. The protective covering of claim 1 in which said membrane has an elongation of at least about 100%.

12. The protective covering of claim 1 in which an absorbent material is provided about the perimeter of said viewing means for taking up water in the area intended to be protected from moisture.

13. The protective covering of claim 12 in which said absorbent material completely encircles the perimeter of said viewing means.

14. The protective covering of claim 12 in which said absorbent material is a super polymer absorbent composition.

15. The protective covering of claim 1 in which said viewing means and said affixing means are integrally formed.

16. The protective covering of claim 1 in which said affixing means includes a continuous band attached to the skin adjacent the perimeter of the delicate features requiring protection from moisture for limited periods of time, said band being adapted to bond to said waterproof flexible membrane.

17. The protective covering of claim 16 in which said continuous band is adapted to adhere to the skin more tightly than to said protective coating.

18. The protective covering of claim 16 wherein the bond is magnetic attraction.

19. The protective covering of claim 1 in which an indicator is provided which changes color upon entry of moisture to the area of the delicate features requiring protection from moisture or trauma.

20. The protective covering of claim 1 in which the membrane is rigid.

21. A protective covering for select areas of the surface anatomy of the body having incisions, wounds, injuries, or other delicate features requiring protection comprising:

a flexible membrane having dome-shaped rigid or semi-rigid means for viewing across said membrane, .said viewing means being sufficiently resistant to deformation to withstand blows without collapsing onto the wound site; and adhesive for affixing said membrane to the select areas of the surface anatomy of the body with said dome-shaped means positioned above the incisions, wounds, injuries, or other delicate features requiring protection.

* * * * *